US008442626B2

(12) United States Patent
Zavoronkovs et al.

(10) Patent No.: US 8,442,626 B2
(45) Date of Patent: May 14, 2013

(54) SYSTEMS AND METHODS FOR COMMUNICATING WITH A COMPUTER USING BRAIN ACTIVITY PATTERNS

(76) Inventors: Aleksandrs Zavoronkovs, Riga (LV); Mikhail Bakhnyan, Moscow (RU)

(*) Notice: Subject to any disclaimer, the term of this patent is extended or adjusted under 35 U.S.C. 154(b) by 318 days.

(21) Appl. No.: 12/819,937

(22) Filed: Jun. 21, 2010

(65) Prior Publication Data

US 2011/0313308 A1 Dec. 22, 2011

(51) Int. Cl.
*A61B 5/04* (2006.01)
(52) U.S. Cl.
USPC .............................. 600/544; 706/20; 382/224
(58) Field of Classification Search .................. 600/544, 600/545; 706/20; 382/224
See application file for complete search history.

(56) References Cited

U.S. PATENT DOCUMENTS

| 5,638,826 | A | 6/1997 | Wolpaw et al. |
| 6,510,340 | B1 | 1/2003 | Jordan |
| 6,904,408 | B1 | 6/2005 | McCarthy et al. |
| 7,529,685 | B2 | 5/2009 | Davies et al. |
| 7,572,234 | B2 | 8/2009 | Viirre et al. |
| 2002/0095099 | A1 | 7/2002 | Quyen et al. |
| 2003/0018278 | A1 | 1/2003 | Jordan |
| 2003/0144857 | A1 | 7/2003 | Lacour et al. |
| 2004/0059241 | A1 | 3/2004 | Suffin |
| 2005/0251419 | A1 | 11/2005 | Suffin et al. |
| 2006/0281996 | A1 | 12/2006 | Kuo et al. |
| 2007/0050715 | A1 | 3/2007 | Behar |
| 2009/0062679 | A1* | 3/2009 | Tan et al. ...................... 600/544 |
| 2009/0063866 | A1 | 3/2009 | Navratil et al. |
| 2009/0137924 | A1* | 5/2009 | Kapoor et al. ................ 600/545 |
| 2009/0282030 | A1 | 11/2009 | Abbott et al. |
| 2009/0292221 | A1 | 11/2009 | Viirre et al. |

* cited by examiner

*Primary Examiner* — Navin Natnithithadha
*Assistant Examiner* — Etsub Berhanu

(57) ABSTRACT

The embodiments described herein are directed to systems and methods for communicating with a computer. The system includes a capture device having sensors to capture a particular brain activity pattern indicative of the mental activity generated in the user by a particular subject, a data storage device operable for storing a plurality of stored brain activity patterns each of which being associated with at least one computer readable indicia indicative of a subject that generated that brain activity pattern. The system also has a processor operable to receive the captured brain activity pattern, search for matching stored brain activity patterns, and if there is at least one matching stored brain activity pattern, retrieve the at least one indicia associated with the at least one matching stored brain activity pattern. The capture device may be an EEG capture device and the captured and stored brain activity patterns are EEG profiles.

30 Claims, 7 Drawing Sheets

SYSTEMS AND METHODS FOR COMMUNICATING WITH A COMPUTER USING BRAIN ACTIVITY PATTERNS

FIELD

The embodiments described herein relate to systems and methods for communication and in particular, to systems and methods for communicating with a computer.

INTRODUCTION

Communication between a user and a computer typically requires the user to express his/her thoughts using a computer input device. Examples of conventional input devices include tactile devices such as keyboards, mice, and touch-sensitive pads. A user may also communicate with a computer audibly using a microphone and speech-recognition software. In some cases, a user may communicate with a computer based on tracking the eye movements of the user.

However, not all individuals may be able to communicate with a computer using conventional methods and devices. Some individuals may have difficulty expressing their thoughts in words. Elderly people with dementia may have trouble finding appropriate words to communicate what they are thinking. Similarly, individuals living with various stages of Alzheimer's disease may also have trouble doing the same. Some individuals may be physically unable to use available input devices. Individuals with severe spinal cord injury often have trouble using most input devices.

In some circumstances, individuals may not be willing to communicate what they are thinking. For example, in a law enforcement or a security-screening context, it may be desirable to obtain some information about an individual's thoughts even if the individual is unwilling to explicitly provide it.

Generally, individuals who think alike tend to get along with each other. As such, it may be desirable to find individuals who think alike to for social or professional networking purposes.

Accordingly, there is a need for improved communicating systems and methods that facilitate communication with computers.

SUMMARY

According to one embodiment of the invention there is provided a system for communicating with a computer. The system includes a capture device wearable by a user, the capture device having sensors to monitor the user's mental activity and to capture a particular brain activity pattern indicative of the mental activity generated in the user by a particular subject. The system also includes at least one data storage device operable for storing a plurality of stored brain activity patterns, each of the stored brain activity patterns being associated with at least one computer readable indicia indicative of a subject that generated that brain activity pattern. The system also includes at least one processor operatively connected to the capture device and the at least one data storage device. The at least one processor is operable to receive the captured brain activity pattern, compare the captured brain activity pattern to each of the plurality of stored brain activity patterns in the data storage device to determine if the captured brain activity pattern matches at least one of the stored brain activity patterns, and if there is at least one matching stored brain activity pattern, retrieve the at least one indicia associated with the at least one matching stored brain activity pattern.

In some embodiments, the capture device comprises an electroencephalogram (EEG) capture device and the brain activity pattern is an EEG profile.

In some embodiments, the computer readable indicia comprises at least one keyword.

In some embodiments, the at least one processor is further operable to use the at least one retrieved keyword to perform at least one of presenting the at least one retrieved keyword using an output device, conducting a search for additional information by submitting the at least one retrieved keyword as a search criteria to a keyword information data storage device, determining a mood of the user based on the at least one keyword and conducting an action to affect the mood of the user, and determining compatibility of the user to another individual based on the similarity of the user's captured EEG profile to the other individual's EEG profile associated with the same at least one retrieved keyword.

in some embodiments, the at least one data storage device comprises a local EEG data storage device and a group EEG data storage device, the local EEG data storage device is operable for storing at least one stored EEG profile and the at least one associated keyword provided by the user, and the group EEG data storage device is operable for storing a plurality of stored EEG profiles and associated keywords provided by a plurality of individuals.

According to another embodiment of the invention, there is provided a method for communicating with a computer. The method comprises the steps of: monitoring a user's mental activity using an capture device coupled to the user, the capture device having sensors to detect a user's mental activity; capturing a particular brain activity pattern indicative of mental activity generated by the user thinking about a particular subject using the capture device; connecting to at least one data storage device containing a plurality of stored brain activity patterns, each of the plurality of stored brain activity patterns being associated with at least one indicia indicative of a subject that generated that brain activity pattern; comparing the captured brain activity pattern to each of the plurality of the stored brain activity patterns to determine if the captured brain activity pattern matches at least one brain activity pattern; and if there is at least one matching brain activity pattern, retrieving the at least one keyword associated with the at least one matching brain activity pattern.

According to another embodiment of the invention, there is provided a method for populating a data storage device with a plurality of indicia. The method comprises the steps of: monitoring a user's mental activity using an capture device coupled to the user, the capture device having sensors to detect a user's mental activity; capturing a particular brain activity pattern indicative of mental activity generated by the user thinking about a particular subject using the capture device; receiving at least one indicia from the user using an input device, the at least one indicia being indicative of the subject that generated the mental activity; associating the at least one indicia with the captured brain activity pattern; storing the captured brain activity pattern and the at least one associated indicia in at least one data storage device; determining whether to captured another brain activity pattern, and if so determined, repeating steps described above.

BRIEF DESCRIPTION OF THE DRAWINGS

The embodiments herein will now be described, by way of example only, with reference to the following drawings, in which.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein.

Furthermore, this description is not to be considered as limiting the scope of the embodiments described herein in any way, but rather as merely describing the implementation of the various embodiments described herein.

In some cases, the embodiments of the systems and methods described herein may be implemented in hardware or software, or a combination of both. However, in some cases, these embodiments are implemented in computer programs executing on programmable computing device each comprising at least one processor, a data storage device (including volatile and non-volatile memory and/or storage elements), at least one input device, and at least one output device.

For example and without limitation, the computing device may be a mainframe computer, a server, a personal computer, a laptop, a personal data assistant, a tablet computer, a smart phone, or cellular telephone. Program code may be applied to input data to perform the functions described herein and generate output information. The output information may be applied to one or more output devices, in known fashion.

Each program may be implemented in a high level procedural or object oriented programming and/or scripting language. However, the programs can be implemented in assembly or machine language, if desired. In any case, the language may be a compiled or interpreted language. Each such computer program may be stored on a non-transitory storage media or a device (e.g. ROM or magnetic diskette) readable by a general or special purpose programmable computer, for configuring and operating the computer when the storage media or device is read by the computer to perform the procedures described herein.

The inventive system may also be considered to be implemented as a computer-readable storage medium, configured with a computer program, where the storage medium so configured causes a computer to operate in a specific and predefined manner to perform at least some of the functions described herein.

Figure 1:
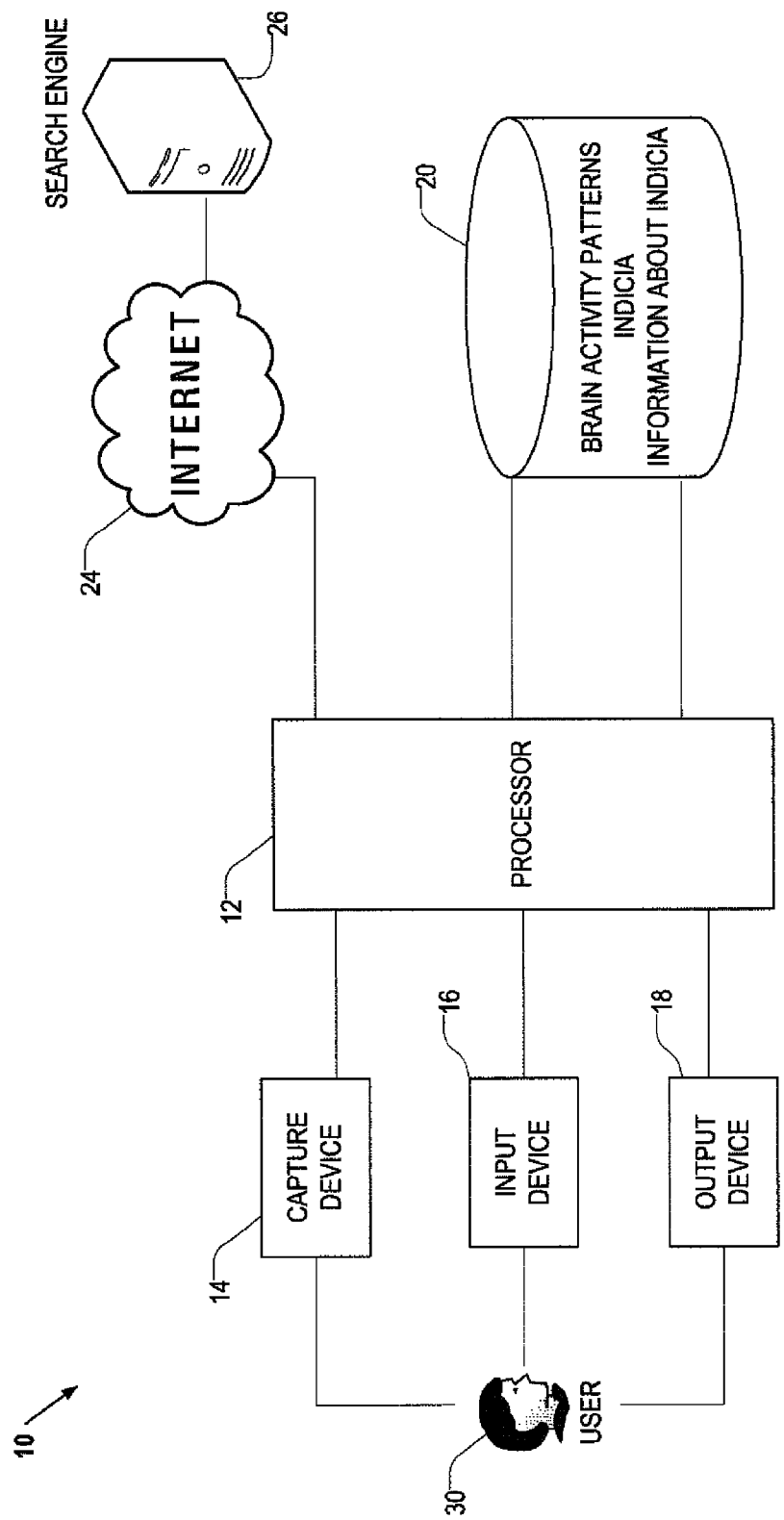
FIG. 1 is a schematic diagram illustrating a system for communicating with a computer according to one embodiment of the invention.

Referring to FIG. 1, illustrated therein is a system 10 for communicating with a computer according to one embodiment of the invention. The system 10 has a processor 12, a capture device 14, an input device 16, an output device 18, a data storage device 20, and a search engine 26.

The processor 12 is operatively coupled to the capture device 14, input device 16, output device 18, data storage device 20, and through the Internet 24 to the search engine 26.

In other embodiments, the type, number, and/or configuration of the components of the system 10 may differ.

The capture device 14 a capture device wearable by a user 30. The capture device having sensors to monitor the user's mental activity and to capture a particular brain activity pattern indicative of the mental activity generated in the user by a particular subject. The subject that generates the mental activity may be any topic that the user can think about. For example, the subject may be an image, a mental event, an emotional state, and/or a person known to the user The processor 12 is operatively connected to the data storage device 20. The data storage device 20 contains a plurality of stored brain activity patterns. Each of the stored brain activity patterns is associated with at least one computer readable indicia indicative of a subject that generated that brain activity pattern. The plurality of stored brain activity patterns and associated indicia may have been previously provided by the user 30 and/or other individuals.

The computer readable indicia may be any computer readable data that is indicative of a subject of a user's thoughts. For example, the indicia may include one or more keywords. The indicia may also include text, images, audio, and/or video files. The indicia may be stored in the local data storage device 20 as instructions executable by the processor 12 to present the indicia in the output device 18.

The local data storage device 20 may also contain additional information about the indicia stored therein. For example, if the subject is a person known to the user, the indicia may be the text "John Doe", and additional information may include contact information and biographical information about the person John Doe.

The processor 12 is operable to receive the captured brain activity pattern from the capture device 14 from the capture device 16. The processor is also operable to compare the captured brain activity pattern to each of the plurality of stored brain activity patterns in the data storage device 20 to determine if the captured brain activity pattern matches at least one of the stored brain activity patterns, and if there is at least one matching stored brain activity pattern, retrieve the at least one indicia associated with the at least one matching stored brain activity pattern.

Once at least one indicia associated is retrieved from the local data storage device 20, the processor 12 may be operable to present the at least one retrieved indicia using the output device 18.

If multiple retrieved indicia is presented, the processor may be further operable to receive an input using the input device 16 to identify which of the presented indicia is indicative of the subject that generated the mental activity.

The processor 12 may also be operable to conduct a search for additional information by submitting the at least one indicia as a search criteria. If one or more indicia is identified as being indicative of the subject, the processor 12 may conduct the search using only those identified indicia as the search criteria. The search may be conducted at the data storage device 20 or the search engine 26.

The processor 12 may also be operable to determine the compatibility of the user to another individual based on the similarity of the user's brain activity pattern to another individual's brain activity pattern that is associated with the same at least one retrieved indicia.

Figure 2:
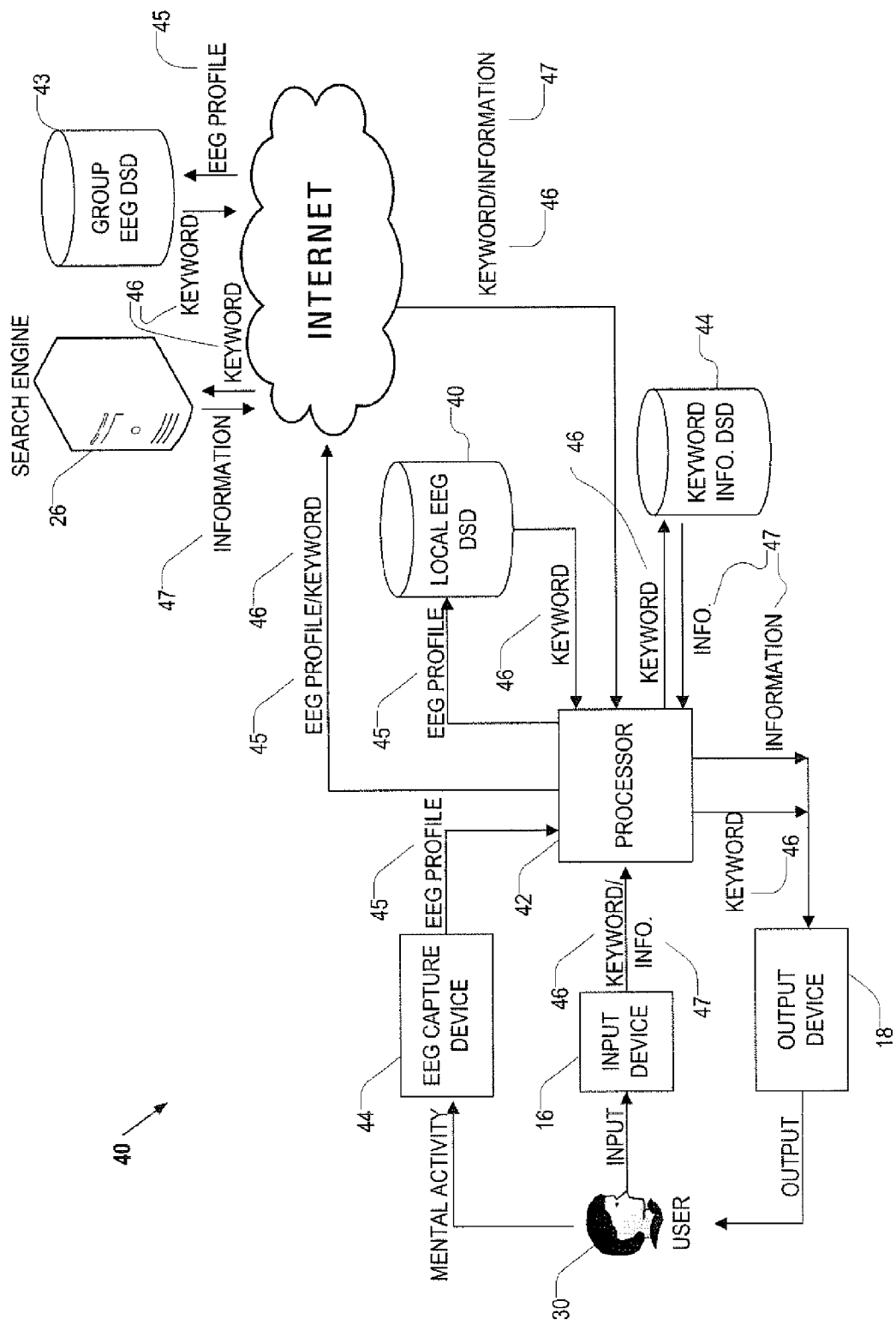
FIG. 2 is a schematic diagram illustrating a system for communicating with a computer according to another embodiment of the invention.

Referring now to FIG. 2, illustrated therein is a system 40 for communicating with a computer according to another embodiment of the invention. The system 40 may be similar to the system 20 in some aspects and like components are indicated by like reference numerals.

The system 40 comprises a processor 42, an EEG capture device 44, an input device 16, an output device 18, a local EEG data storage device 40, a group EEG data storage device 43, a keyword 46 information 47 data storage device 44 and a search engine 26.

The processor 42 is operatively coupled to the EEG capture device 44, input device 16, output device 18, data storage device 20, and through the Internet 24 to the search engine 26.

In other embodiments, the type, number, and/or configuration of the components of the system 40 may differ. For example, there may not be any local EEG data storage device 40 and only one group EEG data storage device 43. In another example, there may not be any keyword 46 information 47 data storage device 44. In another example, there may be more than one processor 42.

The EEG capture device 44 is a device wearable by the user 30. The EEG capture device 44 has EEG sensors to monitor a user's mental activity and to capture an EEG profile 45 indicative of mental activity generated in the user by a subject.

The EEG capture device 44 is typically worn on the head of the user such that the EEG sensors are typically placed on the material locations on the scalp of the user 30.

The shape and form of the EEG capture devices 18 may differ from one to another. For example, each sensor may be individually placed on at each material location on the user's 30 scalp. In another example, the sensors may be incorporated to a wearable device such as a headset-like EEG capture device 44 marketed under the trademark Mindset by NeuroSky Incorporated.

Generally, a more precise placement of the sensors on the user's 30 head will result in more accurate readings. As a shape of an individual's head may differ from individual to individual, it may be desirable to find the locations to place the EEG sensors on an individual-by-individual basis. For example, a medical imaging technique such as a magnetic resonance imaging (MRI) may be applied to a user's head to generate a detailed geometry model of the individual's head. The model may then be used to determine the optimal locations to place the EEG sensors of the EEG capture device 44.

Figure 3:
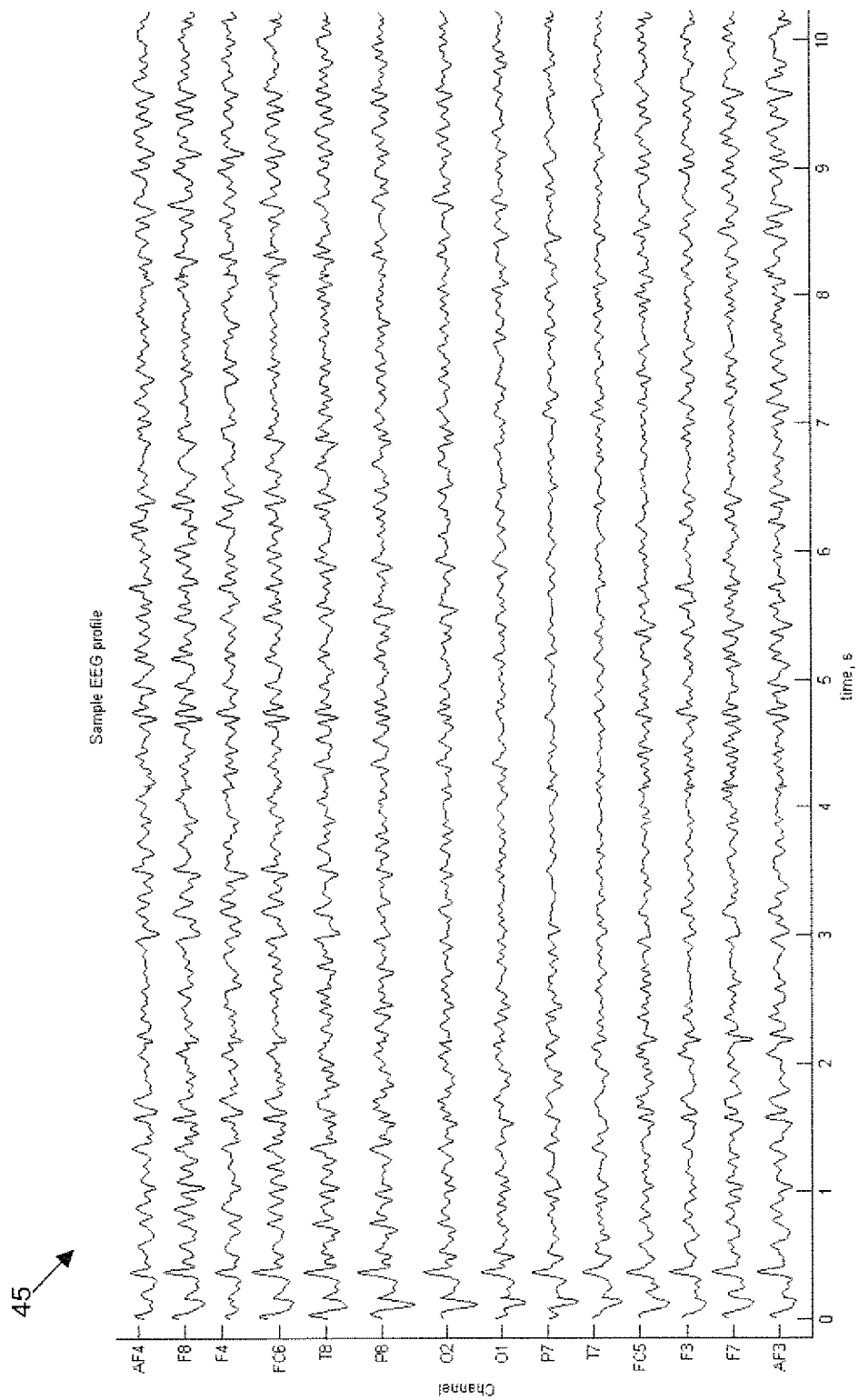
FIG. 3 is an exemplary EEG profile captured by the EEG capture device shown in FIG. 2.

The EEG capture device 44 captures at least one EEG profile 45 having EEG oscillations at various locations and various frequencies over a period of time. For example, illustrated in FIG. 3 is an exemplary EEG profile 45 having oscillations at various channels over a time period of 10 seconds.

The captured EEG profile 45 may differ based on various factors. Generally, a different mental activity may result in a different EEG profile 45 being captured.

For example, if the user 30 is focused and concentrating, the EEG profile 45 captured during the period while the user was concentrating may be different from the EEG profile 45 captured when the user is not concentrating.

The EEG profiles 45 may also differ based on the subject that the user is thinking about. The subject may be any topic that the user can think about that generates a measurable amount of electrical activity within the brain that can be measured by the EEG capture device 44 and captured in an EEG profile 45. For example, the subject may be an image, a mental event, an emotional state, and/or a person known to the user. In another example, the subject may be an image of a hamburger. In another example, the subject may be a relative or an acquaintance of the user 30. In another example, the subject may be a place such as the user's 30 home. In another example, the subject may be an emotional state of the user 30 such as hunger, sadness, or happiness.

Generally, a different subject may generate different mental activity in the user 30, which results in a different EEG profile 45 being captured. For example, an EEG profile 45 that is captured when the user 30 is working a mathematics problem may be different from an EEG profile 45 that is captured when the user 30 is thinking about art.

To capture an EEG profile 45 associated with a specific topic, the user 30 may be presented with a specific subject, for example, using the output device 18 prior to capture.

However, a specific subject need not be presented. For example, the user 30 may be prompted to think about any subject prior to the EEG profile 45 being captured. In another example, the EEG capture device 44 may continuously monitor the EEG profile 45 and capture an EEG profile 45 at regular intervals (e.g. every 10 second).

Generally, the subjects that evoke stronger emotional response or mental concentration from the user may provide greater amount of measurable EEG activity. Also, if the subject that provoked the EEG profile comprises some kind of rhythm (for example, if EEG profile is captured while the user is listening to the music), it could be recognized more robustly.

There may be variances within the captured EEG profiles 45. For example, there may be variances in the captured EEG profiles 45 generated by a same subject within an individual. There may also be variances in captured EEG profiles 45 generated by a same subject between different individuals in a group.

A same subject may generate different EEG profile 45 in the user 30 depending on the context the subject is thought about. For example, if the subject of the user's thoughts is ice-cream, then the EEG profile 45 generated in the user 30 may differ depending on the time of day the EEG profile 45 is captured.

In another example, the EEG profile 45 captured may differ because of inaccuracy in the EEG capture device 44. In another example, the EEG profile 45 captured may differ based on various "noise" associated with the capture. The noise may arise from various factors. For example, the user 30 being unable to maintain his attention on the subject when the EEG profile 45 was captured may generate noise in the captured EEG profile 45.

In another example, EEG profiles 45 generated by a same subject may differ from user to user. For example, if the subject is a "hamburger", the subject may generate a different EEG profile 45 in a vegetarian user in comparison to a non-vegetarian user.

To account for variances, a number of different approaches may be applied. For example, signal filtering, signal averaging, artifact removal, extraction of specific features may be applied to the captured EEG profile 45.

For signal filtering, a standard high-pass filter at 0.5-1 Hz may be applied to filter out slow artifacts such as movement artifacts and electrovoltaic signals. A low-pass filter at 35-70 Hz may also be applied for cleaning out high-frequency electromyographic signals. The signal may be preprocessed using finite impulse response filter prior to applying the high-pass filter and the low-pass filter.

To remove some variances (for e.g. those caused by eye blinks), algorithms based on independent component analysis and blind source separation (ICA-based BSS) may be applied to the captured EEG profile. During classifier learning process an average of the signals corresponding to same stimulus (image, etc.) may be obtained to further suppress variance. During learning process, certain features, such as covariance matrices, wavelet coefficients, etc. are extracted from signal. These features are later stored in database 47 and may be used for classification process.

Depending on the configuration of the system, the above stated approaches to handle variances may be applied by the EEG capture device 44 (either via hardware or software processing) or by the processor 42 once the captured EEG profile 45 is provided to the processor 42. In some embodiments, the above approaches to handle variances may also be applied a processor other than the processor 42 operatively coupled to the group EEG data storage device 43.

The EEG capture device 44 is operatively connected to the processor 42. Depending on the type of the EEG capture device 44, various types of connection software and hardware protocols may be applied to operatively connect the EEG capture device to the processor 42. For example, a universal serial bus (USB), parallel port, IEEE 1394 (Firewire) connections may be used.

The captured EEG profile 45 of the user 30 is communicated to the processor 42. As stated above the processor 42 is operatively connected to the local EEG data storage device 40.

The local EEG data storage device 40 may include volatile and non-volatile computer memory. For example, the data storage device 12 may include random access memory (RAM), magnetic computer storage devices such as hard disk drives, and flash memory.

The local EEG data storage device 40 is operable for having a plurality of stored EEG profiles 45. Each of the plurality of stored EEG profiles 45 has at least one associated keyword 46 of a subject that generated that EEG profile 45 in a user.

The local EEG data storage 20 device may use database management software system to facilitate efficient storage and searching of the stored EEG profiles 45 and associated keywords 46. For example, the local EEG data storage device 40 may be configured as a relational database.

The stored EEG profiles 45 and associated keywords 46 may have been received from various sources. For example, some stored EEG profiles 45 and associated keywords 46 in the local EEG data storage device 40 may have been previously provided by the user 30 using the input device 16. The local EEG data storage device 40 may also have stored EEG profiles 45 and associated keywords 46 of various individuals generated by various subjects. Generally, the local EEG data storage device 40 will store EEG profiles 45 and associated keywords 46 that are relevant to the user 30.

The processor 42 is also operatively connected to the group EEG data storage device 43 via the Internet 24. In other embodiments, other forms of data communication networks may be employed to operatively connect the processor 42 to the group EEG data storage device 43.

The group EEG data storage device 43 may be hosted by a web-server to facilitate communications between to the processor 42 through the Internet 24.

The group EEG data storage device 43 may also have a processor (other than the processor 42) operatively connected therewith, the processor being operable to search the contents of the group EEG data storage device 43. For example, if the group EEG data storage device 43 is connected to a web-server, then there may be a processor on the web-server operatively connected to the group EEG data storage device 43. The processor may receive and execute instructions from various processors connected to it (e.g. the processor 42).

The connection to the group EEG data storage device 43 may be facilitated by a plug-in application in a web browser application. Exemplary web browser applications include Microsoft Internet Explorer, Mozilla Firefox, and Google Chrome.

The group EEG data storage device 43 have stored EEG profiles 45 and associated keywords 46 of a plurality of users generated by a plurality of subjects. Generally, the group EEG data storage device 43 will contain a larger number of EEG profiles 45 and associated keywords 46 in comparison to the local EEG data storage device 40 as the local EEG data storage device 40's contents are more focused on the stored EEG profiles 45 relevant to the user 30.

The group EEG data storage device 43 may be connected to a plurality of users other than the user 30. As such, the group EEG data storage device 43 may function as a centralized repository for various captured EEG profiles 45 and associated keywords 46 from various users. That is, the group EEG data storage device 43 may function as centralized data storage device having a collection of EEG profiles 45 and associated keywords 46 that are accessible by a plurality of users and/or systems.

In other embodiments, there may only be the local EEG data storage device 40. In such cases, at least some of the contents of the group EEG data storage device 43 may be transferred to the local EEG data storage device.

In other embodiments, there may only be the group EEG data storage device 43. In such cases, all the captured EEG profiles 45 will be transferred to the group EEG device for searching and storage purposes.

The processor 42 may be further programmed to transmit one or more of the stored EEG profiles 45 and associated keywords 46 on the local EEG data storage device 40 to the group EEG data storage device 43 from time to time. The contribution of stored local EEG profiles 45 to the group EEG data storage device 43 may help develop the contents of the group EEG data storage device 43.

The stored EEG profiles 45 of various users may be developed on an ongoing basis at the group EEG data storage device 43. Generally, patterns will emerge as more EEG profiles 45 are collected.

EEG profiles 45 stored in the group EEG data storage device 43 may be preprocessed to reduce signal variance. For example, the EEG profiles 45 may be filtered using standard EEG filters and averaged such that an average EEG profile 45 for a plurality of different users associated with a same subject is obtained. Classification parameters, such as covariance matrices, are pre-computed and also stored in the group EEG data storage device 43.

Each of the stored EEG profiles 45 is associated with at least one computer readable keyword 46 that is indicative of a subject that generated the mental activity associated with that stored EEG profile 45.

The keyword 46 is in a computer readable format but is not limited to text. For example, the keyword 46 of a subject may be a number, or instructions in a programming language or format to provide an audio or video playback. For example, a keyword 46 may be the text "HAMBURGER" if EEG profile 45 is captured when the user was thinking about hamburgers. In another example, a keyword 46 may be a phone number and/or a name of a person if the associated EEG profile 45 is captured when the user was thinking about the person.

The association between the EEG profile 45 and the at least one keyword 46 indicative of the subject may be direct or indirect. For example, when the subject thinks about an image depicting a hamburger or a word "hamburger", an EEG profile 45 associated with the user 30 thinking about a hamburger will be captured. The EEG profile 45 may be searched against stored EEG profiles 45 in the database to retrieve the associated keyword 46, which might be the text "hamburger". This is an example of a direct association.

With indirect association, the system 40 performs an additional cognitive association with the retrieved keyword 46 and other stored keywords 46. For example, the retrieved keyword 46 "hamburger" may be indirectly associated with other food items and/or the concept of hunger. These indirect associations may be presented to the user as alternatives for selection.

The processor 42 is also operatively connected to the keyword information data storage device 44. The keyword information data storage device 44 may include volatile and non-volatile computer memory. For example, the keyword information data storage device 44 may include random access memory (RAM), magnetic computer storage devices such as hard disk drives, and flash memory.

The keyword information data storage device 44 has additional information 47 relating to various keywords 46. For example, if the keyword 46 is the text "Hamburger", the related information 47 may include recipes to prepare a hamburger, address and contact information about a restaurant severing hamburgers, or any information that the user 30 may have provided that is associated with the keyword 46. Similarly, if the keyword 46 is the text "John Doe", then the information 47 related to John Doe may include his address, contact numbers, birthday and/or any other information that the user may have provided.

The processor 42 is also operatively connected to the search engine 26 through the Internet 24. The search engine 26 may be an existing Internet search engine web site. For example the search engine 26 may be www.google.com provided by Google Incorporated, www.yahoo.com by Yahoo! Incorporated, and/or www.bing.com by Microsoft Corporation.

The search engine 26 may be used to search for additional information 47 relating to various keywords 46.

A plug-in application to a browser-application may be employed to facilitate communication between the search engine 26 and the processor 42 (or processor 12).

Generally, the in information 47 in the keyword information data storage device is personalized to the user 30 while the information 47 in the search engine 26 is general information about various keywords 46. For example, the information 47 in the keyword information data storage device 44 may include customized information provided by the user 30 relating to various keywords 46.

The output device 18 is operable to present retrieved keyword 46 and/or related information 47 to the user 30. The output device may be a display screen, an audio playback device, or a communication device. In some embodiments, there may be more than one output device 18. For example, the output device 18 may be a LCD screen, a speaker and a cellular phone.

Depending on the type of retrieved keyword 46, related information 47, and desired use of the system 40, various types of output devices may be employed to present the retrieved keyword 46 and/or related information 47 to the user 30. For example, if the retrieved keyword 46 or related information 47 is a phone number, the output device 18 may be a phone and the phone number is presented to the user 30 by dialing the phone. In another example, if the retrieved keyword 46 is in text format, the output device may be a display screen and/or a text-speech translator and an audio output device to audibly present the retrieved keyword 46.

The processor 42 is operable to perform various functions as described herein below. The processor 42 may be coupled to a data storage device (not shown) storing instructions, the instructions being executable by the processor 42 to provide the functionalities. The instructions may be provided in various programming languages including object oriented programming languages.

In other embodiments, there may be more than one processor. For example, the processor 42 may also delegate performance of certain functions to one or more other processors operatively connected to the processor 42. For example, if the group EEG data storage device 43 has a processor other than the processor 42 operatively coupled thereto, the processor 42 may delegate operations involving EEG profiles 45 stored in the group EEG data storage device 43 to that processor.

The processor 42 may be operable in a search mode or a training mode. When operating in the training mode, the processor 10 will create a data storage device having at least one keyword 46 associated with mental activity. That is, the user 30 is attempting to "train" the system 40 to recognize the EEG profiles 45 generated by various subjects on the user 30. When operating in the search mode, the system 40 search for at least one computer readable keyword 46 associated with a mental activity, and if applicable, information 47 relating to the at least one keyword 46.

In some embodiments, in the search mode the processor 42 may be operable to perform some steps of the method 50 for communicating to a computer illustrated in FIGS. 4 and 5 as described herein below.

In the search mode, the processor 42 is operable to receive the captured EEG profile 45 from the EEG capture device 44. The processor 42 compares the captured EEG profile 45 to each stored EEG profile 45 in the local EEG data storage device 40 and the group EEG data storage device 43 to determine if the captured EEG profile 45 matches one or more of the stored EEG profiles 45. If there are one or more matching stored EEG profiles 45 profiles, the processor 42 is further operable to retrieve the at least one keyword 46 associated with the one or more matching stored EEG profiles 45, and present the retrieved keyword 46 using the output device.

The processor 42 may search for stored EEG profiles 45 that match the captured EEG profiles 45 in one or both of the local EEG data storage device 40 and the group EEG data storage device 43. To improve efficiency in some circumstances, the search may be conducted on the local EEG data storage device 40 initially and the group EEG data storage device 43 only if the initial search did not yield desired results.

To compare the captured EEG profile 45 with the stored EEG profiles 45, the processor 42 may be operable to execute pattern recognition algorithms such as the Common Spatial Pattern algorithm which is described in an article by Muller-Gerking et. al "Designing Optimal Spatial Filters for Single-Trial EEG Classification in a Movement Task" (Clinical Neurophysiology, Vol. 110, No. 5, pp. 787-798).

Other algorithms in addition to, instead of, and/or adapting the Common Spatial Pattern algorithm may also be used to facilitate efficient matching of the captured EEG profile 45 to the stored EEG profiles 45 in the EEG data storage device.

The EEG profiles 45 may be classified to facilitate searches. For example, algorithms such as Hidden Markov Modes, Support Vector Machines, Neural Networks or modification of such algorithms may be used to classify the EEG profiles 45 and facilitate searches of EGG profiles 45.

The processor 42 may be further operable to calculate a similarity value for each stored EEG profile 45, the similarity value being indicative of the similarity of each stored EEG profile 45 to the captured EEG profile 45. The similarity value may be used by the processor 42 to determine if the captured profile matches one or more of the stored EEG profiles 45 when the processor 42 is operating in the search mode.

For example, for each stored EEG profile 45 that is being compared to the captured EEG profile 45, a real number similarity value between 0 and 1 may be assigned. A similarity value of 0 suggests that there is no similarity between the EEG profiles 45 being compared while a similarity value of 1 indicates high degree of similarity or exact match between the compared EEG profiles 45. Majority of the stored EEG profiles 45 that are being compared will likely result in a similarity value between 0 and 1, which indicates a partial match. To determine whether a partial match should be considered a "match" (for the purpose of presenting to the user or searching for related information 47), a threshold value may be determined for each subject. For example, a "match" value indicative the degree of similarity between the stored EEG profile 45 and the captured EEG profile 45 to generate a match may be calculated based on user feedback as described herein below.

The processor 42 may be operable to conduct a search for additional information 47 by submitting the at least one keyword 46 as a search criteria to at least one keyword 46 information 47 data storage device. In the embodiment as shown, the processor 42 is operable to conduct one or more searches in both the keyword 46 information 47 data storage device 44 and the Internet search engine 26.

A number of factors could be used to determine whether to search for additional related information 47. For example, there may be instructions saved with the at least one retrieved keyword 46 to present that keyword 46 or to search for additional related information 47. In another example, if there are more than one retrieved keywords 46, it may be desirable to present the retrieved keywords 46 to the user for selection prior to searching for additional related information 47. In another example, whether to present the retrieved keyword 46 to a user could be determined from the type of the at least one retrieved keyword 46 (e.g. if the keyword 46 is an audio file, then present it). In addition, if there are indirect associations with the at least one retrieved keyword 46, they may also be presented to the user 30 for selection.

The processor 42 may present the at least one retrieved keywords 46 prior to searching for additional related information 47 using the output device 18. After presenting the keywords 46 associated with the matching profiles using the output 18, the processor 42 may be further operable to receive input to identify which of the retrieved keywords 46 are indicative of the subject that generated the mental activity. For example, the keywords 46 "hamburger", "food", "hunger", and "Joe's burger shop" associated with four matching stored EEG profiles 45 may be presented. The user 30 may provide input as to which of the keywords 46 presented is indicative the subject that he was thinking about when the captured EEG profile 45 was generated. For example, the user 30 may select "Joe's burger shop" as the most accurate indication of what he was thinking about. The user 30 may use the input device 14 to input his selection. In another example, the user may select more than one keyword 46 as being indicative of the subject that he was thinking about.

In the embodiment as shown, the processor 42 is operable to connect to at least one keyword 46 information 47 data storage device 44 storing a plurality of keywords 46 and related information 47. The processor 42 is also operable to connect to an Internet search engine 26. After connecting to the keyword 46 information 47 data storage device 44, the processor 42 may also conduct a search for information 47 related to the at least one retrieved keyword 46 by using the at least one retrieved keyword 46 as a search constraint in the keyword 46 information 47 data storage device 44 and/or the search engine 26. If related information 47 is located, the processor 42 is operable to obtain the related information 47 and present the related information 47 using the output device 18.

The processor 42 may be operable to conduct the search using only the retrieved keywords 46 identified by the input as being indicative of the subject that generated the mental activity. To continue the previous example, the processor 42 may only search the keywords 46 "Joe's burger" because that is the only keyword 46 identified by the user 30 as being indicative of the subject that generated the captured EEG profile 45.

The processor 42 may also be operable to compare the similarity of the captured EEG profile 45 to the stored EEG profile 45 that is associated with the at least one retrieved keyword 46 as identified by the user to determine a degree of similarity between those profiles. Based on similarity, the processor 42 may generate a match value for that stored EEG profile 45 indicative of the degree of similarity between that stored EEG profile 45 and the captured EEG profile 45 required to generate a match.

The match value indicates the degree of similarity required between two EEG profiles 45 to generate a match when comparing the profiles. This value may be useful for accounting for variances between two EEG profiles 45. For example, a same subject may generate two EEG profiles 45 that are not identical to each other from the same user 30. The match value indicates the degree of difference permitted between the two EEG profiles 45 and still be considered as a match when comparing the profiles.

In some embodiments, the processor 42 may be operable to determine compatibility of the user 30 to another individual based on the similarity of the user's captured EEG profile 45 to the other individual's EEG profile 45, both the captured and stored EEG profiles 45 being associated with the same at least one retrieved keyword 46.

For example, the processor 42 may be operable to perform some steps of the method 150 for creating a data storage device having at least one keyword 46 associated with mental activity of a user illustrated in FIGS. 6 and 7 and described herein below.

In addition to receiving the captured EEG profile 45 from the EEG capture device 44, the processor 42 may be operable to receive at least one keyword 46 from the user 30 using an input device 14. The at least one keyword 46 is indicative of the subject that generated the mental activity. The processor 42 will associate the at least one keyword 46 with the captured EEG profile 45, and store the captured EEG profile 45 and the at least one associated keyword 46 at in the local EEG data storage device 40.

The processor 42 may be further operable to provide the captured EEG profile 45 and the at least one associated keyword 46 stored in the local EEG data storage device 40 to the group EEG data storage device 43. In some embodiments, a plug-in application to a web browser application may be used to facilitate the transmission.

The processor 42 may be further operable to receive additional information 47 related to at least one keyword 46 from the user using an input device. The processor 42 may also be operable to associate the additional information 47 to the at least one keyword 46, and store the additional information 47 in the at least one keyword information data storage device 44.

In other embodiments, various methods to improve quality of captured EEG profiles 45 may be employed. For example, prior to saving a captured EEG profile 45 in the local EEG profile 45 data storage device 30, the user may be asked to recall the subject again to generate a second captured EEG profile 45. The second captured EEG profile 45 may be compared against the first EEG profile 45 to determine a similarity value and a match value.

General signal quality is taken into account when an EEG profile 45 is captured. For example, frequency distribution of captured EEG profile is used to assess how similar captured signal to normal EEG signal. Considerable deviations in frequency distribution may be indicative improper positioning of the EEG sensors or otherwise improper usage of the EEG capture device 44. If such deviations are detected, the processor 42 may be operable to inform the user to confirm proper positioning or usage of the EEG capture device 44.

Figure 4:
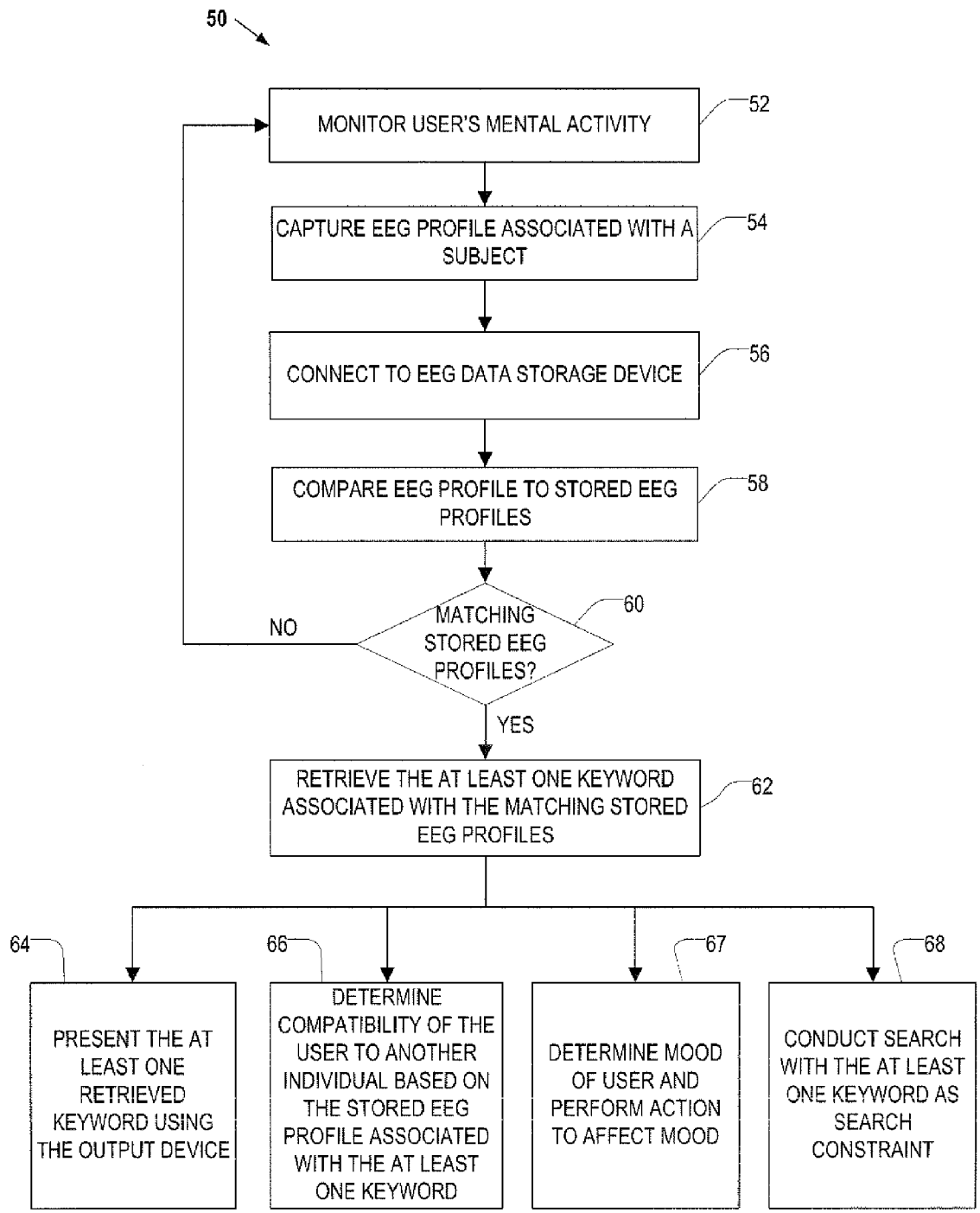
FIG. 4 a flow chart illustrating the steps in a method for communicating with a computer according to another embodiment of the invention.

Referring now to FIG. 4, illustrated therein is a method 50 for communicating with a computer. Each of the steps of the method 50 may be implemented by one or more of the components of the system 40 as described herein above. For example, some of the steps indicated below may be performed by a processor such as the processor 12 of the system 40.

At step 52, the method 50 monitors a user's mental activity using an EEG captured device coupled to the user. The EEG capture device may be the EEG capture device 14 as described herein above.

At step 54, the method 50 captures an EEG profile indicative of a mental activity generated by the user thinking about a subject using the EEG capture device. The EEG profile and the subject may be the same as the EEG profile and the subject in system 40 as described above.

At step 56, the method 50 connects to at least one data storage device. The at least one EEG data storage device contains a plurality of stored EEG profiles and associated computer readable keywords. Each of the stored EEG profile is associated with at least one keyword, and each keyword is indicative of a subject that generated the mental activity associated with that stored EEG profile. The at least one EEG data storage device may be the local EEG data storage device 40 and/or the group EEG data storage device 43 in system 40 as described herein above. The EEG profiles may be the EEG profiles 45, and the computer readable keywords may be the keywords 46 as described above.

At step 58, the method 50 compares the captured EEG profile to each of the plurality of the stored EEG profiles to determine if the captured profile matches one or more of the stored EEG profiles. To determine whether there are one or more matching stored EEG profiles, the method 50 may use various pattern recognition algorithms or other algorithms that are used by the processor 42 as described herein above.

At step 60, the method 50 determines if there are any stored EEG profiles that matches the captured EEG profile. If there is at least one matching stored EEG profile, the method proceeds to step 62. If there are no matching stored EEG profiles, the method returns to step 52.

At step 62, the method 50 retrieves the at least one keyword associated with the at least one matching stored EEG profile from the at least one EEG data storage device.

If at least one associated keyword is retrieved, the method 50 may perform at least one of the optional steps 64, 66, 67 or 68 as described below.

At step 64, the method 50 presents the at least one retrieved keyword using an output device. The output device may be a device such as the output device 18 in system 40. This step may be performed if the method 50 is being performed to assist an individual with formulating his or her thoughts into words. This step may be performed if there are multiple matching stored EEG profiles and user input is desirable to determine which of the matching stored EEG profiles are indicative of the user's thoughts.

At step 66, the method 50 may determine compatibility of the user to another individual based on the similarity of the user's captured EEG profile to the other individual's EEG profile. This is based on the premise that individuals who generate more similar EEG profiles to the same subjects may be more psychological "compatible" with each other than with participants who generates less similar EEG profiles to the same subjects. For example, a plurality of users may be exposed to a same set of subjects to generate EEG profiles. The users with the most similar EEG profiles to the same subjects may be viewed as being more compatible than the users with less similar EEG profiles. The compatibility as determined by the method may be used for social and/or professional networking purposes.

At step 67, the method 50 determines the mood of the user based on the keyword retrieved and conduct an action to affect the mood of the user. For example, if the retrieved keyword indicates that the user is tired and sleepy, the method 50 switch off computers/lights etc. In another example, if the user wishes to stay awake in spite of drowsiness, the method 50 may generate sound or lights to keep the user awake. In another example, the method 50 may play calming music if the keyword retrieved indicates that the user is under stress. In other embodiments, the retrieved keyword may be associated with one or more actions to be performed without determining the mood of the user.

At step 68, the method 50 may conduct a search for additional information by submitting the at least one keyword as a search criteria to at least one keyword information data storage device. The additional information may be the information 47 as described in system 40 herein above.

In some embodiments, the method 50 may perform steps 102-114 illustrated in FIG. 5 and described below instead of step 68 to search for additional information relating the at least one retrieved keywords.

Figure 5:
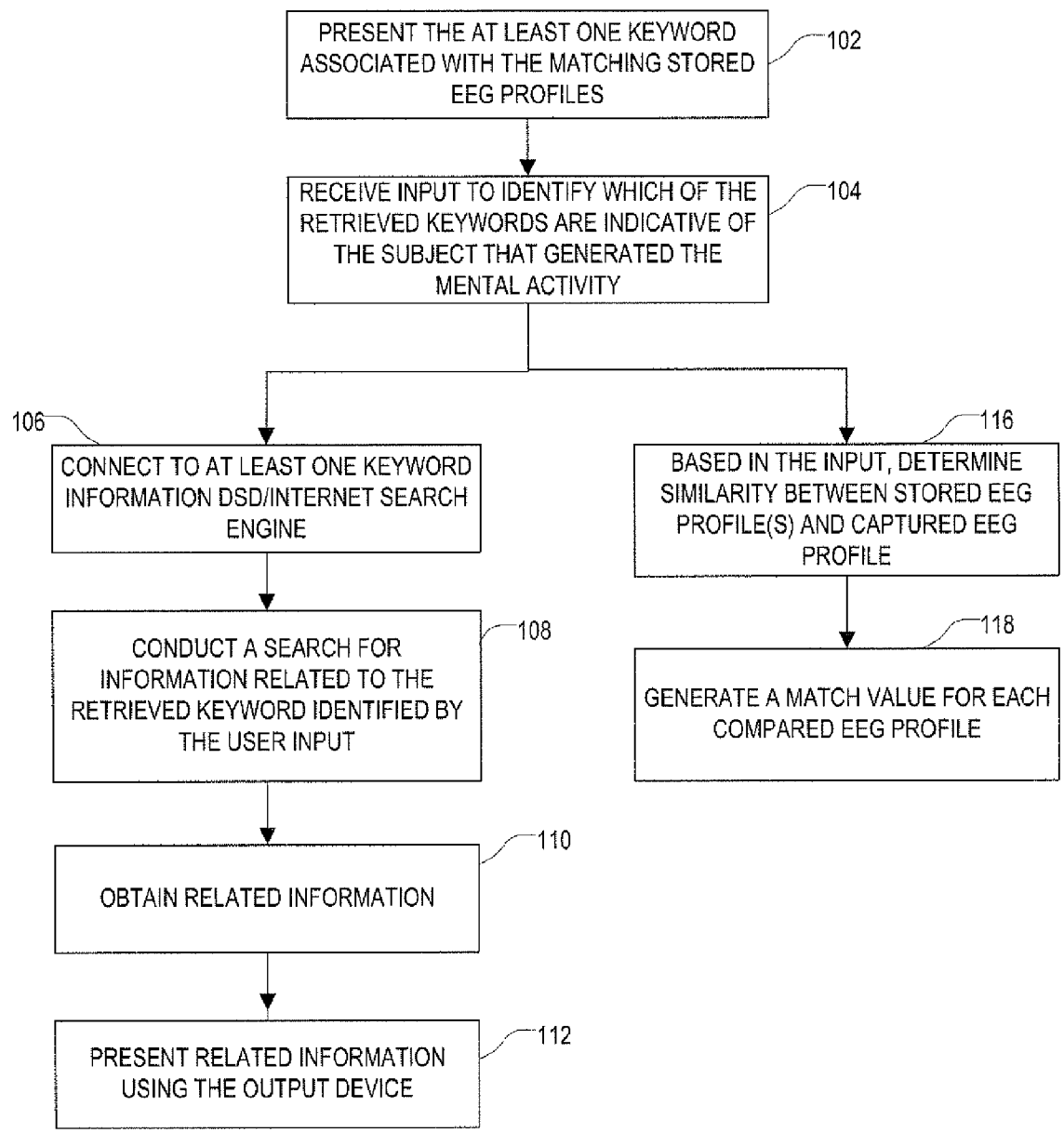
FIG. 5 is a flow chart illustrating additional steps that may be performed by the method shown in FIG. 4 in some embodiments.

Referring now to FIG. 5, at step 102, the method 50 will present the at least one retrieved keyword using the output device. If multiple keywords are retrieved, then the keywords will be presented in a form that permits user to select one or more of the keywords. For example, the keywords may be presented as a list on a display screen.

At step 104, the method 50 will receive input to identify which of the at least one retrieved keywords are indicative of the subject that generated the mental activity. For example, the method 50 may receive input via an input device such as mouse clicks from a user to indicate which of the retrieved keywords accurately indicate the subject that the user was thinking about when the capture EEG profile was generated. If the input indicates that none of the presented keywords accurately indicate the subject, then the method 50 may return to step 52.

At step 106, the method 50 connects to at least one keyword information data storage device. The keyword information data storage device may be a data storage such as the keyword information data storage device 44 of the system 40 as described above. The keyword information data storage device contains a plurality of stored keywords and related information. In some embodiments, the method 50 may connect to an Internet search engine such as the Internet search engine 26 as described above.

At step 108, the method 50 conducts a search for information related to the at least one retrieved keyword by using the at least one retrieved keyword as a search constraint in the at least one keyword information data storage device and/or the Internet search engine. If the input received at step 104 identify certain keywords as being indicative of the subject that generated the captured mental activity, only those identified keywords will be used to search for additional information.

At step 110, the method 50 obtains additional information related to the at least one retrieved keywords that were used to conduct the search.

At step 112, the method 50 presents the additional information obtained in step 110 using the output device.

In some embodiments, the method 50 may also perform steps 116 and 118 to generate a match value for each EEG profile which has at least one associated keyword identified by the input received in step in step 104. The match value is indicative of a degree of similarity required to generate a match between a stored EEG profile and another profile. In other words, the match value indicates an amount of variance permitted between two EEG profiles generated by a same subject.

At step 116, the method 50 will determine which of the stored EEG profiles are associated with the presented keywords what are identified by the input received step 104. The method 50 will then determine the similarity between each of these stored EEG profiles and the captured EEG profile.

At step 118, the method 50 will generate a match value for each of the stored EEG profiles identified in step 116 based on the similarity determined in step 116. The match values may be stored in the at least one EEG data storage device.

The method 50 in the embodiment as described is directed to using EEG profiles and associated keywords to communication with a computer. In other embodiments, other forms of brain activity patterns and associated indicia may be used.

Figure 6:
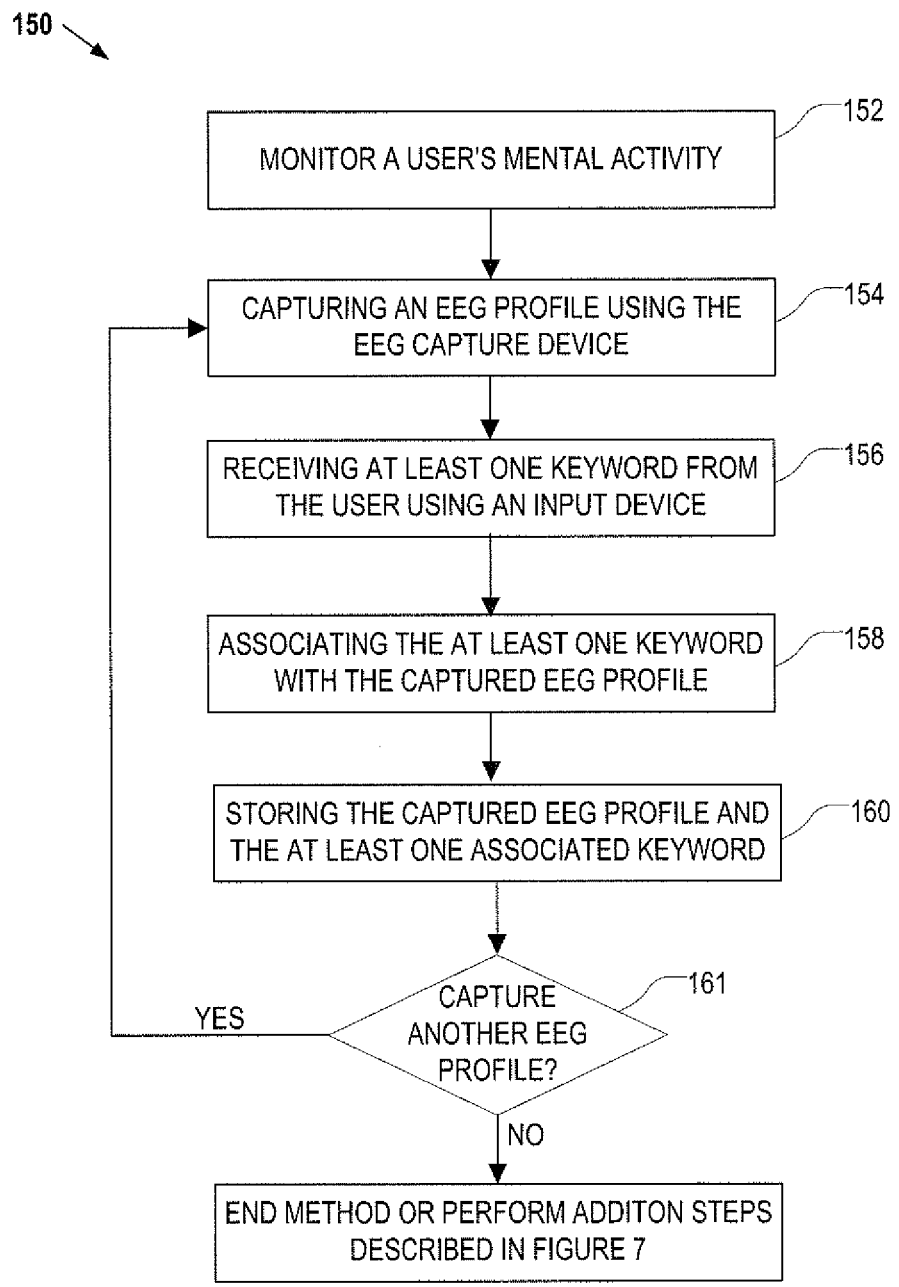
FIG. 6 is a flow chart illustrating the steps in a method for populating a data storage device with a plurality of indicia according to another embodiment of the invention.

Referring now to FIG. 6, illustrated therein is a method 150 for populating a data storage device with a plurality of keywords. The steps of method 150 may be performed by one or more of the components of system 40 described herein above.

At step 152, the method 150 monitors the mental activity of the user by coupling an EEG capture device to the user. The EEG capture device may be a device such as the EEG capture device 48 of the system 40 as described herein above.

At step 154, the method 150 captures an EEG profile indicative of the user's mental activity generated by the user thinking about a particular subject using the EEG capture device. The captured EEG profile may be the same as the captured EEG profile 45 described above in system 40.

At step 156, the method 150 receives at least one keyword from the user using an input device. The input device may be a device such as the input device 14 of system 40. The at least one keyword is indicative of the subject that generated the mental activity and may be the same as the keyword 46 of the system 10 as described above.

At step 158, the method 150 associates the at least one keyword with the captured EEG profile.

At step 160, the method 150 stores the captured EEG profile and the at least one associated keyword at in at least one EEG data storage device. The at least one EEG data storage device may be a data storage device such as the local EEG data storage device 40 or the group EEG data storage device 43 of system 40 as described herein above.

At step 161, the method 150 determines whether to capture another EEG profile. For example, a user input may be solicited to determine whether to capture another EEG profile. In another example, the method 150 may automatically determine whether to capture another EEG profile without any user input. If it is determined that another EEG profile should be captured, the method returns to step 154. If it is determined that the method will not capture another EEG profile, the method 150 may end, or in some embodiments, perform optional steps 162 to 166 shown in FIG. 7.

Figure 7:
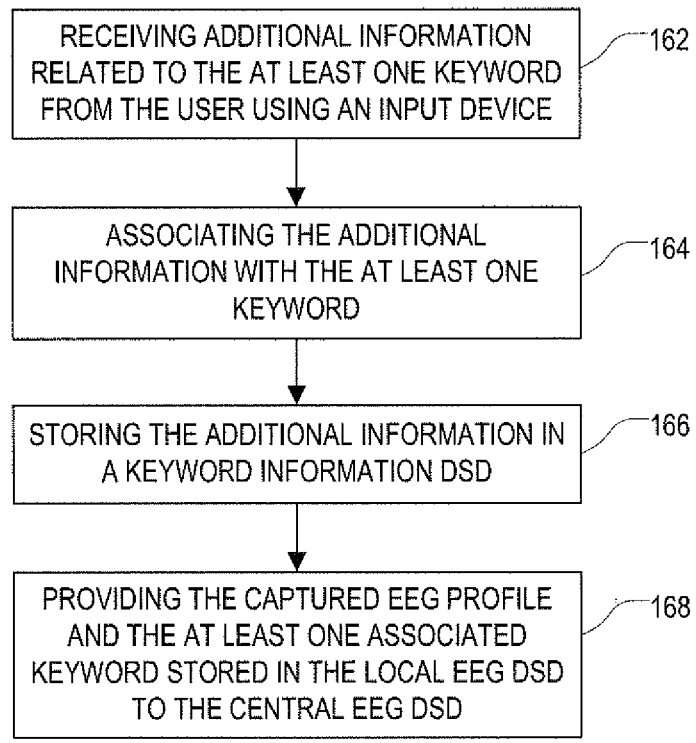
FIG. 7 is a flow chart illustrating additional steps that may be performed by the method shown in FIG. 6 in some embodiments.

Referring now to FIG. 7, illustrated therein are steps to receive and store additional information about one or more keywords and updating a group EEG data storage device. At step 162 the method 150 receives additional information related to the keywords using the input device. The additional information may be the same as the additional information 47 in system 40 as described herein above.

At step 164, the method 150 associates the additional information with the keywords.

At step 166, the method 150 stores storing the additional information in a keyword information data storage device. The keyword information data storage device may be a data storage device such as the keyword information data storage device 44 described herein above.

In some embodiments where there is a local EEG data storage device and a group EEG data storage device, the method 150 may also perform step 168 to provide data to the group EEG data storage device.

At step 168, the method 150 stores the captured EEG profile and the at least one associated keyword at in the local EEG data storage device.

The method 150 in the embodiment as described above is directed to populating an EEG data storage device with a plurality of EEG profiles and associated keywords. In other embodiments, the method may be executed to populate a data storage device other forms of brain activity patterns and associated indicia.

While the steps of the above methods have been described sequentially hereinabove, it should be noted that sequential performance of the steps may not need to occur for successful implementation of the method. As will be evident to one skilled in the art, rearranging sequence of performance of the steps, omitting the performance of some steps, adding additional steps or performing the steps in parallel may be possible without abandoning the essence of the invention.

In some embodiments, the systems and methods for EEG profiling may be used as a tool to assist with interrogation of a user. The captured EEG profile of the user can be analyzed to detect features that correspond to normal physiological reactions of human to psychological stress (e.g. telling lies). The captured EEG profile may also indicate whether the user has previous knowledge of the subject that was presented. The system may also be used to display keyword associated with the user's current thoughts, which may be helpful to determine whether the user should be subject to further interrogation.

While certain embodiments have been illustrated and described herein, many modifications, substitutions, and changes can be made to these embodiments without departing from the present invention, the scope of which is defined in the appended claims

The invention claimed is:

1. A system for communicating with a computer comprising:
   a) a capture device wearable by a user, the capture device having sensors to monitor the user's mental activity and to capture a particular brain activity pattern indicative of the mental activity generated in the user by a particular subject, wherein the capture device comprises an electroencephalogram (EEG) capture device and the captured brain activity pattern is a captured EEG profile;
   b) at least one data storage device operable for storing a plurality of stored EEG profiles, each of the stored EEG profiles being associated with at least one computer readable indicia indicative of a subject that generated that EEG profile, wherein the computer readable indicia comprises at least one keyword;
c) at least one processor operatively connected to the capture device and the at least one data storage device, the at least one processor being operable to:
 i) receive the captured EEG profile,
 ii) compare the captured EEG profile to each of the plurality of stored EEG profiles in the data storage device to determine if the captured EEG profile matches at least one of the stored EEG profiles, and
 iii) if there is at least one matching stored EEG profile, retrieve the at least one keyword associated with the at least one matching stored EEG profile,
d) at least one keyword information data storage device operatively connected to the at least one processor, the keyword information data storage device storing information relating to various keywords; and
e) wherein when at least one keyword associated with the captured EEG profile is retrieved, the at least one processor is further operable to:
 i) connect to the at least one keyword information data storage device,
 ii) conduct a search at the at least one keyword information data storage device using the at least one retrieved keyword as a search constraint for information related to the at least one retrieved keyword,
 iii) if related information is located, obtain the related information associated with the retrieved keywords, and
 iv) present the related information using an output device.

2. The system according to claim 1, wherein when there are a plurality of matching stored EEG profiles, the at least one processor is further operable to:
 a) receive an input to identify which of the retrieved keywords are indicative of the subject that generated the mental activity; and
 b) conduct the search only using the retrieved keywords identified by the input as being indicative of the subject that generated the mental activity.

3. The system according to claim 1 further comprising an input device operatively connected to the at least one processor, and the processor being further operable to:
 a) receive at least one keyword from the user using the input device, the at least one keyword being indicative of the subject that generated the mental activity;
 b) associate the at least one keyword with the captured EEG profile; and
 c) store the captured EEG profile and the at least one associated keyword in the at least one data storage device.

4. The system according to claim 3, wherein the at least one data storage device comprises a local EEG data storage device and a group EEG data storage device, the local EEG data storage device is operable for storing at least one stored EEG profile and the at least one associated keyword provided by the user, and the group EEG data storage device is operable for storing a plurality of stored EEG profiles and associated keywords provided by a plurality of individuals.

5. The system according to claim 4, wherein the at least one processor is further operable to provide the captured EEG profile and the at least one associated keyword stored in the local EEG data storage device to the group EEG data storage device.

6. The system according to claim 3, wherein the processor is further operable to:

a) receive additional information related to at least one keyword from the user using an input device;
b) associate the additional information to the at least one keyword; and
c) store the additional information in the at least one keyword information data storage device.

7. The system according to claim 1, wherein the processor is further operable to:
 a) calculate a similarity value for each stored EEG profile, the similarity value being indicative of the similarity of each stored EEG profile to the captured EEG profile, and
 b) determine if the captured profile matches one or more of the stored EEG profiles based on the similarity value.

8. A system for communicating with a computer comprising:
 a) a capture device wearable by a user, the capture device having sensors to monitor the user's mental activity and to capture a particular brain activity pattern indicative of the mental activity generated in the user by a particular subject, wherein the capture device comprises an electroencephalogram (EEG) capture device and the captured brain activity pattern is a captured EEG profile;
 b) at least one data storage device operable for storing a plurality of stored EEG profiles, each of the stored EEG profiles being associated with at least one computer readable indicia indicative of a subject that generated that EEG profile, wherein the computer readable indicia comprises at least one keyword; and
 c) at least one processor operatively connected to the capture device and the at least one data storage device, the at least one processor being operable to:
  i) receive the captured EEG profile,
  ii) compare the captured EEG profile to each of the plurality of stored EEG profiles in the data storage device to determine if the captured EEG profile matches at least one of the stored EEG profiles, and
  iii) if there is at least one matching stored EEG profile, retrieve the at least one keyword associated with the at least one matching stored EEG profile;
 d) wherein the at least one processor is further operable to:
  i) connect to at least one Internet search engine storing a plurality of stored keywords and related information,
  ii) conduct a search at the Internet search engine using the at least one retrieved keyword as a search constraint for related information,
  iii) if related information is located, obtain the related information associated with the retrieved keywords, and
  iv) present the related information using an output device.

9. The system according to claim 8, wherein when there are a plurality of matching stored EEG profiles, the at least one processor is further operable to:
 a) receive an input to identify which of the retrieved keywords are indicative of the subject that generated the mental activity; and
 b) conduct the search only using the retrieved keywords identified by the input as being indicative of the subject that generated the mental activity.

10. The system according to claim 8 further comprising an input device operatively connected to the at least one processor, and the processor being further operable to:
 a) receive at least one keyword from the user using the input device, the at least one keyword being indicative of the subject that generated the mental activity;
 b) associate the at least one keyword with the captured EEG profile; and c) store the captured EEG profile and the at least one associated keyword in the at least one data storage device.

11. The system according to claim 10, wherein the at least one data storage device comprises a local EEG data storage device and a group EEG data storage device, the local EEG data storage device is operable for storing at least one stored EEG profile and the at least one associated keyword provided by the user, and the group EEG data storage device is operable for storing a plurality of stored EEG profiles and associated keywords provided by a plurality of individuals.

12. The system according to claim 11, wherein the at least one processor is further operable to provide the captured EEG profile and the at least one associated keyword stored in the local EEG data storage device to the group EEG data storage device.

13. The system according to claim 10, further comprising at least one keyword information data storage device, wherein the processor is further operable to:
   a) receive additional information related to at least one keyword from the user using an input device;
   b) associate the additional information to the at least one keyword; and
   c) store the additional information in the at least one keyword information data storage device.

14. The system according to claim 8, wherein the processor is further operable to:
   a) calculate a similarity value for each stored EEG profile, the similarity value being indicative of the similarity of each stored EEG profile to the captured EEG profile, and
   b) determine if the captured profile matches one or more of the stored EEG profiles based on the similarity value.

15. A system for communicating with a computer comprising:
   a) a capture device wearable by a user, the capture device having sensors to monitor the user's mental activity and to capture a particular brain activity pattern indicative of the mental activity generated in the user by a particular subject, wherein the capture device comprises an electroencephalogram (EEG) capture device and the captured brain activity pattern is a captured EEG profile;
   b) at least one data storage device operable for storing a plurality of stored EEG profiles, each of the stored EEG profiles being associated with at least one computer readable indicia indicative of a subject that generated that EEG profile, wherein the computer readable indicia comprises at least one keyword; and
   c) at least one processor operatively connected to the capture device and the at least one data storage device, the at least one processor being operable to:
      i) receive the captured EEG profile,
      ii) compare the captured EEG profile to each of the plurality of stored EEG profiles in the data storage device to determine if the captured EEG profile matches at least one of the stored EEG profiles, and
      iii) if there is at least one matching stored EEG profile, retrieve the at least one keyword associated with the at least one matching stored EEG profile;
   d) wherein when the at least one retrieved keyword is presented to the user, the processor is further operable to:
      i) receive an input from the user to indicate whether the at least one retrieved keyword is indicative of the subject that generated the captured profile,
      ii) based on the input from the user, compare the captured EEG profile to the stored EEG profile that is associated with the at least one retrieved keyword to determine a degree of similarity between those profiles, and
      iii generate a match value for that stored EEG profile indicative of the degree of similarity between that stored EEG profile and the captured EEG profile required to generate a match.

16. The system according to claim 15, wherein when there are a plurality of matching stored EEG profiles, the at least one processor is further operable to:
   a) receive an input to identify which of the retrieved keywords are indicative of the subject that generated the mental activity; and
   b) conduct the search only using the retrieved keywords identified by the input as being indicative of the subject that generated the mental activity.

17. The system according to claim 15, further comprising an input device operatively connected to the at least one processor, and the processor being further operable to:
   a) receive at least one keyword from the user using the input device, the at least one keyword being indicative of the subject that generated the mental activity;
   b) associate the at least one keyword with the captured EEG profile; and
   c) store the captured EEG profile and the at least one associated keyword in the at least one data storage device.

18. The system according to claim 17, wherein the at least one data storage device comprises a local EEG data storage device and a group EEG data storage device, the local EEG data storage device is operable for storing at least one stored EEG profile and the at least one associated keyword provided by the user, and the group EEG data storage device is operable for storing a plurality of stored EEG profiles and associated keywords provided by a plurality of individuals.

19. The system according to claim 18, wherein the at least one processor is further operable to provide the captured EEG profile and the at least one associated keyword stored in the local EEG data storage device to the group EEG data storage device.

20. The system according to claim 17, further comprising at least one keyword information data storage device, wherein the processor is further operable to:
   a) receive additional information related to at least one keyword from the user using an input device;
   b) associate the additional information to the at least one keyword; and
   c) store the additional information in the at least one keyword information data storage device.

21. The system according to claim 15, wherein the processor is further operable to:
   a) calculate a similarity value for each stored EEG profile, the similarity value being indicative of the similarity of each stored EEG profile to the captured EEG profile, and
   b) determine if the captured profile matches one or more of the stored EEG profiles based on the similarity value.

22. A method for communicating with a computer comprising the steps of:
   a) monitoring a user's mental activity using a capture device coupled to the user, the capture device having sensors to detect a user's mental activity, wherein the capture device comprises an electroencephalogram (EEG) capture device;
   b) capturing a particular brain activity pattern indicative of mental activity generated by the user thinking about a particular subject using the capture device, wherein the captured brain activity pattern comprises a captured EEG profile;

c) connecting to at least one data storage device containing a plurality of stored EEG profiles, each of the plurality of stored EEG profiles being associated with at least one computer readable indicia indicative of a subject that generated that EEG profile, wherein the computer readable indicia comprises at least one keyword; using at least one processor, and d) comparing the captured EEG profile to each of the plurality of the stored EEG profiles to determine if the captured EEG profile matches at least one EEG profile;

e) if there is at least one matching EEG profile, retrieving the at least one keyword associated with the at least one matching EEG profile;

f) connecting to at least one keyword information data storage device containing a plurality of stored keywords and related information;

g) conducting a search for additional information related to the at least one retrieved keyword by using the at least one retrieved keyword as a search criteria in the at least one keyword information data storage device;

h) if related information is located, obtaining the related information associated with the at least one retrieved keyword; and i) presenting the related information using an output device.

23. The method according to claim 22, wherein when there is a plurality of matching stored EEG profiles, the method further comprises the steps of:

j) presenting the at least one retrieved keyword using an output device;

k) receiving input to identify which of the at least one retrieved keywords are indicative of the subject that generated the mental activity; and l) conducting the search only using the retrieved keywords identified by the input as being indicative of the subject that generated the mental activity.

24. The method according to claim 22 further comprising the steps of:

j) calculating a similarity value for each stored EEG profile, the similarity value being indicative of the similarity of each stored EEG profile to the captured EEG profile; and k) determining if the captured profile matches one or more of the stored EEG profiles based on the similarity value.

25. A method for communicating with a computer comprising the steps of:

a) monitoring a user's mental activity using a capture device coupled to the user, the capture device having sensors to detect a user's mental activity, wherein the capture device comprises an electroencephalogram (EEG) capture device;

b) capturing a particular brain activity pattern indicative of mental activity generated by the user thinking about a particular subject using the capture device, wherein the captured brain activity pattern comprises a captured EEG profile;

c) connecting to at least one data storage device containing a plurality of stored EEG profiles, each of the plurality of stored EEG profiles being associated with at least one computer readable indicia indicative of a subject that generated that EEG profile, wherein the computer readable indicia comprises at least one keyword; using at least one processor and d) comparing the captured EEG profile to each of the plurality of the stored EEG profiles to determine if the captured EEG profile matches at least one EEG profile;

e) if there is at least one matching EEG profile, retrieving the at least one keyword associated with the at least one matching EEG profile;

f) connecting to at least one Internet search engine containing a plurality of stored keywords and related information;

g) conducting a search for additional information related to the at least one retrieved keyword by using the at least one retrieved keyword as a search criteria in the search engine;

h) if related information is located, obtaining the related information associated with the at least one retrieved keyword; and i) presenting the related information using an output device.

26. The method according to claim 25, wherein when there is a plurality of matching stored EEG profiles, the method further comprises the steps of:

j) presenting the at least one retrieved keyword using an output device;

k) receiving input to identify which of the at least one retrieved keywords are indicative of the subject that generated the mental activity; and l) conducting the search only using the retrieved keywords identified by the input as being indicative of the subject that generated the mental activity.

27. The method according to claim 25, further comprising the steps of:

j) calculating a similarity value for each stored EEG profile, the similarity value being indicative of the similarity of each stored EEG profile to the captured EEG profile; and k) determining if the captured profile matches one or more of the stored EEG profiles based on the similarity value.

28. A method for communicating with a computer comprising the steps of:

a) monitoring a user's mental activity using an capture device coupled to the user, the capture device having sensors to detect a user's mental activity, wherein the capture device comprises an electroencephalogram (EEG) capture device;

b) capturing a particular brain activity pattern indicative of mental activity generated by the user thinking about a particular subject using the capture device, wherein the captured brain activity pattern comprises a captured EEG profile;

c) connecting to at least one data storage device containing a plurality of stored EEG profiles, each of the plurality of stored EEG profiles being associated with at least one computer readable indicia indicative of a subject that generated that EEG profile, wherein the computer readable indicia comprises at least one keyword; using at least one processor and d) comparing the captured EEG profile to each of the plurality of the stored EEG profiles to determine if the captured EEG profile matches at least one EEG profile; and e) if there is at least one matching EEG profile, retrieving the at least one keyword associated with the at least one matching EEG profile;

f) wherein when the at least one retrieved keyword is presented to the user, the method further comprises the steps of:

i) receiving an input from the user to indicate whether the at least one retrieved keyword is indicative of the subject that generated the captured profile;
ii) based on the input from the user, comparing the captured EEG profile to the stored EEG profile that is associated with the keywords identified by the input to determine a degree of similarity between those profiles; and
iii) generating a match value for that stored EEG profile indicative of the degree of similarity between that stored EEG profile and the captured EEG profile required to generate a match.

29. The method according to claim 28, wherein when there is a plurality of matching stored EEG profiles, the method further comprises the steps of:
g) presenting the at least one retrieved keyword using an output device;
h) receiving input to identify which of the at least one retrieved keywords are indicative of the subject that generated the mental activity; and
i) conducting the search only using the retrieved keywords identified by the input as being indicative of the subject that generated the mental activity.

30. The method according to claim 28, further comprising the steps of:
g) calculating a similarity value for each stored EEG profile, the similarity value being indicative of the similarity of each stored EEG profile to the captured EEG profile; and
h) determining if the captured profile matches one or more of the stored EEG profiles based on the similarity value.

* * * * *